United States Patent [19]
Brow et al.

[11] Patent Number: 5,648,302
[45] Date of Patent: Jul. 15, 1997

[54] SEALING GLASSES FOR TITANIUM AND TITANIUM ALLOYS

[75] Inventors: Richard K. Brow; Howard L. McCollister; Carol C. Phifer, all of Albuquerque, N. Mex.; Delbert E. Day, Rolla, Mo.

[73] Assignee: Sandia Corporation, Albuquerque, N. Mex.

[21] Appl. No.: 713,294

[22] Filed: Sep. 13, 1996

[51] Int. Cl.⁶ .............................. C03C 3/068; C03C 3/15
[52] U.S. Cl. .................. 501/50; 501/14; 501/51; 501/78; 428/432; 428/433
[58] Field of Search .................. 501/50, 51, 78, 501/14, 15; 428/432, 433

[56] References Cited

U.S. PATENT DOCUMENTS

| | | | |
|---|---|---|---|
| 3,081,178 | 3/1963 | Weissenberg et al. | 501/78 |
| 4,643,634 | 2/1987 | Kondo et al. | 428/432 |
| 4,945,071 | 7/1990 | Friesen | 501/41 |
| 5,057,378 | 10/1991 | Nishino et al. | 428/432 |
| 5,104,738 | 4/1992 | Brow | 428/433 |
| 5,104,755 | 4/1992 | Taylor | 429/181 |
| 5,137,849 | 8/1992 | Brix | 501/15 |
| 5,176,747 | 1/1993 | Panzera et al. | 501/14 |
| 5,264,287 | 11/1993 | Grebe et al. | 428/433 |

OTHER PUBLICATIONS

H. Rawson and E. P. Denton, "The Glass Sealing Properties of Titanium and Zirconium," *British Journal of Applied Physics*, vol. 5, pp. 352–353, Oct. 1954.

D. R. Salmi and B. C. Bunker, *Glass Corrosion in Liquid Lithium*, Sandia National Laboratories Report No. SAND83-2314, Sep. 1984.

R. K. Brow and R.D. Watkins, "Reactions and Bonding Between Glasses and Titanium," in *Technology of Glass, Ceramic, or Glass–Ceramic to Metal Sealing*, W.E. Moddeman, C. W. Merten, and D.P. Kramer, editors (The American Society of Mechanical Engineers, New York) pp. 25–30, 1987 No Month.

*Primary Examiner*—Karl Group
*Attorney, Agent, or Firm*—John P. Hohimer

[57] ABSTRACT

Barium lanthanoborate sealing-glass compositions are provided comprising various combinations (in terms of mole-%) of boron oxide ($B_2O_3$), barium oxide (BaO), lanthanum oxide ($La_2O_3$), and at least one other oxide selected from the group consisting of aluminum oxide ($Al_2O_3$), calcium oxide (CaO), lithium oxide ($Li_2O$), sodium oxide ($Na_2O$), silicon dioxide ($SiO_2$), or titanium dioxide ($TiO_2$). These sealing-glass compositions are useful for forming hermetic glass-to-metal seals with titanium and titanium alloys having an improved aqueous durability and favorable sealing characteristics. Examples of the sealing-glass compositions are provided having coefficients of thermal expansion about that of titanium or titanium alloys, and with sealing temperatures less than about 900° C., and generally about 700°–800° C. The barium lanthanoborate sealing-glass compositions are useful for components and devices requiring prolonged exposure to moisture or water, and for implanted biomedical devices (e.g. batteries, pacemakers, defibrillators, pumps).

19 Claims, 1 Drawing Sheet

SEALING GLASSES FOR TITANIUM AND TITANIUM ALLOYS

This invention was made with Government support under Contract No. DE-AC04-94AL85000 awarded by the U.S. Department of Energy. The Government has certain rights in the invention.

FIELD OF THE INVENTION

The present invention relates to sealing-glass compositions for forming glass-to-metal seals and, in particular, to sealing-glass compositions for forming hermetic glass-to-metal seals with titanium and titanium alloys.

BACKGROUND OF THE INVENTION

Titanium and titanium alloys have a number of outstanding properties, including high strength-to-weight ratios and excellent resistances to chemical attack, that make them desirable materials for many component applications in the aerospace and biomedical industries. The usefulness of titanium and titanium alloys for component or device design has been limited by the lack of a viable commercial hermetic sealing technology. Titanium undergoes deleterious reactions with commercial silicate-based sealing glasses to form an interfacial silicide reaction product that produces a very weak bond.

Boroaluminate glasses as disclosed in U.S. Pat. No. 5,104,738 to Brow et al are potential candidates for titanium glass-to-metal seals since they have a coefficient of thermal expansion close to that of titanium, and provide glass-to-metal seals with a mechanical strength exceeding that of seals formed from the commercial silicate sealing glasses. A drawback to the boroaluminate glasses, however, is their relatively poor aqueous durabilities which limit, in particular, both in vivo applications (e.g. for implanted batteries, heart pacemakers, defibrillators, pumps or the like) and applications requiring prolonged contact with moisture or water.

Thus, there is a need for improved titanium sealing-glass compositions having an aqueous durability sufficiently high to permit the formation of glass-to-metal seals that are resistant to moisture, water or body fluids (e.g. for in vivo use). There is a further need for improved titanium sealing-glass compositions having favorable viscosity characteristics for forming glass-to-metal seals with titanium or titanium alloys at a sealing temperature below about 900° C. and with little or no tendency for crystallization.

An advantage of the titanium sealing-glass compositions according to the present invention is that a glass-to-metal seal can be formed by a sealing-glass body in contact with a titanium or titanium alloy to provide an aqueous durability that exceeds that of boroaluminate glasses by up to an order of magnitude or more.

Another advantage of the present invention is that the titanium sealing-glass compositions according to the present invention have a glass transition temperature less than about 600° C. so that the glasses can be sealed at a temperature below an allotropic $\alpha$-$\beta$ phase transition temperature of pure titanium near 882° C.

A further advantage is that the titanium sealing-glasses of the present invention have favorable viscosity characteristics at a preferred sealing temperature of about 700°–800° C. for fusing to titanium or a titanium alloy without any need for weights or the like (e.g. weighted graphite fixtures placed above the sealing glasses to promote a flow of the sealing glasses) to aid in seal formation.

Still another advantage is that the titanium sealing-glass compositions of the present invention can be used for forming titanium glass-to-metal seals for in vivo applications including implantable batteries, pacemakers, defibrillators and pumps.

These and other advantages of the titanium sealing glasses of the present invention will become evident to those skilled in the art.

SUMMARY OF THE INVENTION

A family of sealing-glass compositions is provided having an improved aqueous durability for forming glass-to-metal seals with titanium or a titanium alloy. These sealing-glass compositions are barium lanthanoborate with added oxides, including alkali oxides, alkaline-earth oxides, titanium dioxide, aluminum oxide, and silicon dioxide. In particular, the family of titanium sealing-glass compositions according to the present invention comprises boron oxide ($B_2O_3$) in the amount of 40–70 mole-%; barium oxide (BaO) in the amount of 5–30 mole-%; lanthanum oxide ($La_2O_3$) in the amount of 5–20 mole-%; and at least one oxide selected from the group consisting of aluminum oxide ($Al_2O_3$) in the amount of 0–20 mole-%; calcium oxide (CaO) in the amount of 0–12 mole-%; lithium oxide ($Li_2O$) in the amount of 0–8 mole-%; sodium oxide ($Na_2O$) in the amount of 0–8 mole-%; silicon dioxide ($SiO_2$) in the amount of 0–8 mole-%; and titanium dioxide ($TiO_2$) in the amount of 0–15 mole-%. Examples of the titanium sealing-glass compositions of the present invention are provided with coefficients of thermal expansion near that of titanium or titanium alloys, and with a sealing temperature of less than about 900° C., and generally in the range of about 700°–800° C. The titanium sealing-glass composition is useful for forming hermetic glass-to-metal seals with an improved aqueous durability (e.g. for providing a feedthrough for one or more electrical connections of a device that is exposed to moisture, water or body fluids) and with favorable viscosity characteristics for forming glass-to-metal seals without a need for weighted fixtures or the like.

Other advantages and novel features of the invention will become apparent from the following detailed description thereof when considered in conjunction with the accompanying drawings.

BRIEF DESCRIPTION OF THE DRAWINGS

The accompanying drawings, which are incorporated into and form a part of the specification, illustrate several aspects of the present invention and, together with the description, serve to explain the principles of the invention. The drawings are only for the purpose of illustrating preferred embodiments of the invention and are not to be construed as limiting the invention. In the drawings.

DETAILED DESCRIPTION OF THE INVENTION

Figure 1:
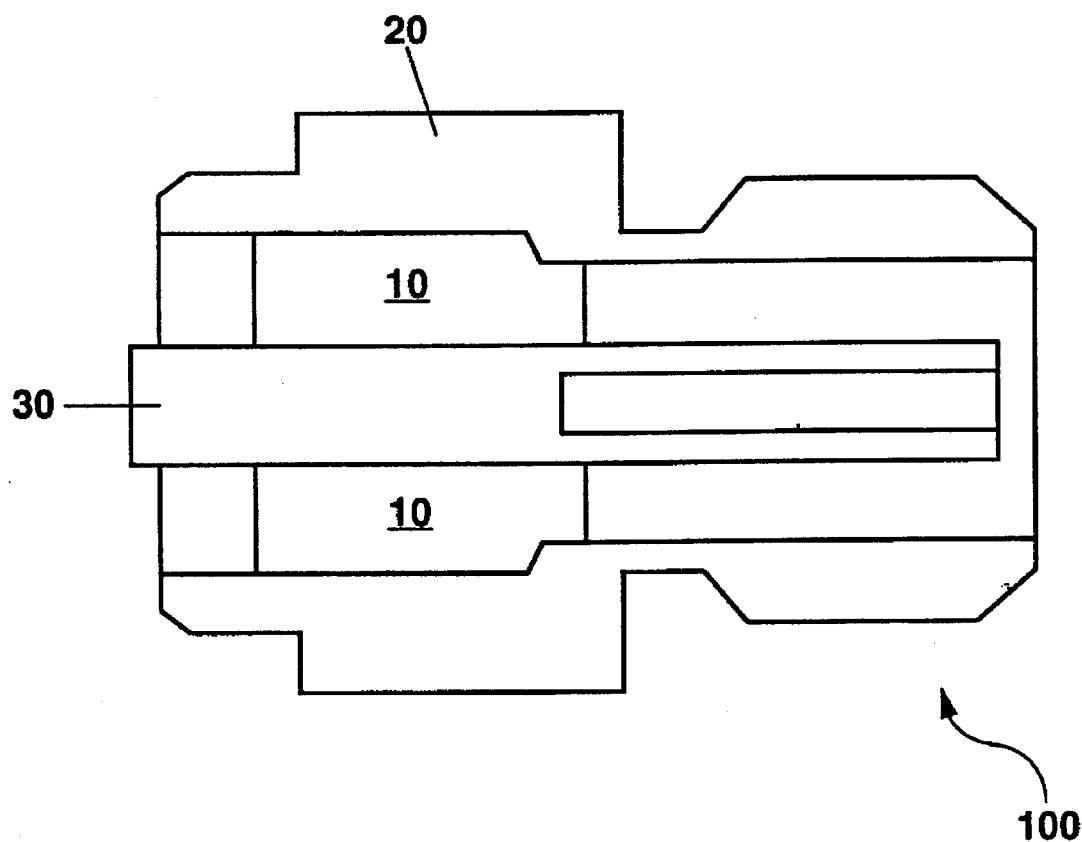
FIG. 1 shows a schematic cross-section diagram of an example of a glass-to-metal seal formed with a titanium sealing-glass composition of the present invention in contact with titanium or a titanium alloy.

The titanium sealing glasses of the present invention comprise barium lanthanoborate compositions with a variety of additional oxides added to modify various glass properties. Compositional ranges for constituent oxides of the barium lanthanoborate sealing glasses (also referred to herein as titanium sealing glasses) of the present invention are listed below in Table 1:

TABLE 1

Compositional Ranges for Barium Lanthanoborate Sealing Glasses

| Oxide | Compositional Range (mole-%) |
|---|---|
| $B_2O_3$ | 40–70 |
| BaO | 5–30 |
| $La_2O_3$ | 5–20 |
| $Al_2O_3$ | 0–20 |
| CaO | 0–12 |
| $Li_2O$ | 0–8 |
| $Na_2O$ | 0–8 |
| $SiO_2$ | 0–8 |
| $TiO_2$ | 0–15 |

The above oxides upon fusing produce glass compositions having thermal expansion characteristics that are substantially matched to titanium and titanium alloys for forming glass-to-metal seals thereto.

The barium lanthanoborate sealing-glass compositions of the present invention can be prepared from predetermined amounts of reagent grade raw materials in the above compositional ranges, including boric acid ($H_3BO_3$) and oxides of barium (e.g. $BaCO_3$), lanthanum ($La_2O_3$), calcium (e.g. $CaCO_3$), lithium (e.g. $Li_2CO_3$), sodium (e.g. $Na_2CO_3$), silicon ($SiO_2$) and titanium ($TiO_2$). The oxides other than $B_2O_3$, BaO, and $La_2O_3$ in a particular titanium sealing-glass composition of the present invention can be used to modify various properties of the composition and to make the composition structurally complex to help prevent crystallization. $Li_2O$ and $Na_2O$ can be used as fluxing agents and to reduce a glass transition temperature, $T_g$, for a particular titanium sealing-glass composition. CaO can be used to adjust a coefficient of thermal expansion (CTE) for a particular titanium sealing-glass composition, since the CTE increases with the ratio of BaO to CaO. The addition of a small amount of $SiO_2$ to the titanium sealing-glass composition improves the glass stability and helps to prevent crystallization of the glass.

Particular titanium sealing-glass compositions of the present invention can be formed, for example, by melting raw materials in the above compositional ranges in a platinum crucible in air at about 1400° C. for about five hours. As formed, the titanium sealing-glass compositions are homogeneous and generally clear.

From the glass melt, sealing-glass preforms of a predetermined size can be formed by casting into preheated molds, or by machining from melt-cast rods. The sealing-glass preforms are then preferably annealed for about 15–20 minutes at or near the glass transition temperature, $T_g$, which can be determined by differential thermal analysis (DTA). Glass-to-metal seals can then be formed from the sealing-glass compositions of the present invention (i.e. from the sealing-glass preforms) in contact with titanium or a titanium alloy using conventional seal-forming techniques in either a continuous belt or batch furnace. Particular sealing-glass compositions according to the present invention can have a coefficient of thermal expansion (CTE) that is within about 5% of that of titanium or a titanium alloy (the CTE of Ti and Ti-alloys is about $90$–$100 \times 10^{-7}$ °C.$^{-1}$) as measured, for example, by dilatometry (e.g. with a dual pushrod dilatometer over a temperature range of generally 50°–500° C.).

Examples of particular titanium sealing-glass compositions according to the present invention are provided in Table 2 together with measured thermal properties and a dissolution rate which provides a measure of the aqueous durability. In Table 2, a crystallization temperature, $T_x$, is provided for each glass composition as determined from an onset of exothermic peaks by differential thermal analysis (DTA). In general, the titanium sealing-glass compositions have a glass transition temperature, $T_g$, of less than about 600° C.; and a crystallization temperature, $T_x$, that is about 150° to 270° C. higher than the glass transition temperature, $T_g$. A large temperature difference, $T_x$–$T_g$, is advantageous for improving the sealability of the glasses by improving the viscosity characteristics of the glasses and preventing crystallization of the glasses before an adequate glass flow has occurred. Sealing (i.e. formation of a glass-to-metal seal with titanium or a titanium alloy by fusing of a glass thereto) is generally performed by heating the sealing glasses to a temperature of about 150°–200° C. above $T_g$.

TABLE 2

Analyzed Composition (mole-%) and Properties of Examples of Barium Lanthanoborate Sealing-Glasses

| Glass Composition | BLB-8 | BLB-9 | BLB-10 | BLB-12 | TIG-23M |
|---|---|---|---|---|---|
| $B_2O_3$ (mold-%) | 63.3 | 65.0 | 55.0 | 54.0 | 44.0 |
| BaO (mole-%) | 20.7 | 15.0 | 20.0 | 9.0 | 9.0 |
| $La_2O_3$ (mole-%) | 5.0 | 10.0 | 5.0 | 8.0 | 10.0 |
| $Al_2O_3$ (mole-%) | 5.0 | 0.0 | 5.0 | 4.0 | 10.0 |
| CaO (mole-%) | 0.0 | 0.0 | 0.0 | 9.0 | 9.0 |
| $Li_2O$ (mole-%) | 3.0 | 5.0 | 5.0 | 5.0 | 5.0 |
| $Na_2O$ (mole-%) | 3.0 | 0.0 | 5.0 | 0.0 | 0.0 |
| $SiO_2$ (mole-%) | 0.0 | 5.0 | 0.0 | 0.0 | 2.0 |
| $TiO_2$ (mole-%) | 0.0 | 0.0 | 5.0 | 11.0 | 11.0 |
| $T_g$ (°C.) | 533 | 584 | 506 | 562 | 561 |
| $T_x$ (°C.) | 800 | 739 | 677 | 765 | 832 |
| CTE ($\times 10^{-7}$ °C$^{-1}$) | 94 | 87 | 103 | 90 | 92 |
| Dissolution Rate (g-cm$^{-2}$min$^{-1}$) | $3.2 \times 10^{-6}$ | $2.5 \times 10^{-7}$ | $6.0 \times 10^{-7}$ | $3.9 \times 10^{-7}$ | $1.8 \times 10^{-7}$ |

In Table 2, the dissolution rates for each titanium sealing-glass composition are determined from weight-loss measurements on polished glass samples after submersion in deionized water at 70° C. for generally about two weeks. A smaller dissolution rate for a particular sealing-glass composition correlates with an increased resistance of the sealing-glass composition to chemical attack by moisture, water, or body fluids containing water (i.e. an increased aqueous durability).

The hermeticity of the titanium sealing-glass compositions according to the present invention can be measured by forming a glass-to-metal seal 100 comprising one or more sealing-glass bodies 10 in contact with a metal comprising titanium or a titanium alloy. Titanium in the form of commercially pure grade 2 (i.e. ≧99% purity) titanium, for example, can be used to form a glass-to-metal seal 100 for use in corrosive environments due to its high chemical durability. Pure titanium, however, exhibits an allotropic α-β phase transition at 882° C. that can degrade the original mechanical properties. Thus, a sealing-glass composition according to the present invention should have a sealing temperature, $T_{seal}$, that is less than about 900° C., and preferably less than 882° C. when used for forming a glass-to-metal seal with pure titanium.

Alternately, a titanium alloy can be used for forming a glass-to-metal seal according to the present invention. For example, a titanium beta C alloy (also referred to herein as Ti-βC) is useful since this titanium alloy is stabilized against the α-β phase transition, thereby allowing the sealing temperature, $T_{seal}$, to exceed 882° C., if necessary. Such a titanium-βC alloy is also useful for certain component or device applications in providing a room-temperature tensile strength on the order of 900 MPa. The term "titanium" as used herein refers to titanium or any alloy thereof.

FIG. 1 shows an example of a glass-to-metal seal 100 according to the present invention. In FIG. 1, the glass-to-metal seal 100 comprises a cylindrical body 10 of an electrically-insulating sealing-glass composition according to the present invention contacting on an outer surface thereof a cylindrical metal shell 20 formed of titanium, and contacting on an inner surface thereof a cylindrical electrical lead pin 30 (i.e. an electrical feedthrough) formed of titanium with an opening at one end thereof for attachment of an electrical wire. Only one of the shell 20 or pin 30 need be made of titanium or a titanium alloy; and the other of the shell 20 or pin 30 can comprise another metal having favorable characteristics for fusing to the titanium sealing glass (e.g. the electrical lead pin 30 can be formed of molybdenum, platinum, or alloy-52 comprising about 52 weight-% nickel and about 48 weight-% iron).

In the example of FIG. 1, the cylindrical glass body 10 can have an outer diameter of about ¼ inch and a width of about ¼ inch. A preform for the glass body 10 can be assembled together with the shell 20 and pin 30 in an alignment fixture (e.g. formed of graphite) and then heated in a continuous-belt or batch furnace in an inert ambient to form the glass-to-metal seal 100 upon cooling. In a continuous-belt furnace, nitrogen can be used as the inert ambient, and the sealing temperature, $T_s$, can be, for example, about 735° C.; whereas, in a batch furnace argon can be as the inert ambient, and $T_s$ can be, for example, about 725° C. In either case, the time required for fusing the glass body 10 to the shell 20 and pin 30 is generally about 10–15 minutes, without any requirement for a weighted fixture to aid flow of the titanium sealing glass.

The glass-to-metal seal 100 can then be slowly cooled down to room temperature in a cool-down process step that preferably includes an annealing step whereby the glass-to-metal seal 100 is annealed for a predetermined period of time (e.g. about 15 minutes) at a temperature near the glass transition temperature, $T_g$, (e.g. about 500°–580° C.). The exact times and temperatures for forming the glass-to-metal seal 100 and the cool-down and annealing steps can be determined from practice of the present invention to provide a glass-to-metal seal 100 that is hermetic and substantially free from crystallization or other defects that can impair the hermeticity or mechanical strength of the seal 100. The completed glass-to-metal seal 100 can be welded or sealed to a container or the like for forming a particular device. Those skilled in the art will know that many different and diverse types of components and devices can be formed according to the teaching of the present invention.

Glass-to-metal seals 100 formed from the various titanium sealing-glass compositions in Table 2 can be evaluated for hermeticity by helium leak detection, with the titanium sealing-glass compositions in Table 2 being hermetic to <$10^{-9}$ cm$^3$-sec$^{-1}$ of helium. The integrity of the glass-to-metal seals 100 can also be tested by a repeated thermal shock cycling of the seals 100 between −50° C. and +150° C., with the glass-to-metal seals 100 formed according to the present invention remaining hermetic after three such thermal shock cycles.

The aqueous durability of the titanium sealing-glass compositions of the present invention can be compared with boroaluminate glasses as disclosed in U.S. Pat. No. 5,104,738 to Brow et al and having compositions and properties as listed in Table 3. The aqueous durability of the barium lanthanoborate sealing glasses of the present invention generally exceeds that of the boroaluminate sealing glasses in Table 3 by about an order of magnitude or more as determined by comparing the measured dissolution rates. A lower dissolution rate equates with a higher aqueous durability.

TABLE 3

Analyzed Composition and Properties of Boroaluminate Sealing-Glasses

| Glass Composition | SrBAl-1 | BaBAl-2 | CaBAl-17 |
| --- | --- | --- | --- |
| CaO (mole-%) | 0 | 0 | 50 |
| SrO (mole-%) | 45 | 0 | 0 |
| BaO (mole-%) | 0 | 40 | 0 |
| Al$_2$O$_3$ (mole-%) | 15 | 20 | 20 |
| B$_2$O$_3$ (mole-%) | 40 | 40 | 30 |
| $T_g$ (°C.) | 575 | 542 | 592 |
| $T_x$ (°C.) | 805 | — | ~800 |
| Coefficient of Thermal Expansion (x $10^{-7}$ °C$^{-1}$) | 98 | 104 | 91 |
| Dissolution Rate (g-cm$^{-2}$min$^{-1}$) | 2.0 × $10^{-4}$ | 1.0 × $10^{-5}$ | 1.0 × $10^{-6}$ |

The improved aqueous durabilities of the titanium sealing-glass compositions of the present invention in Tables 1 and 2 makes these titanium sealing glasses more useful for in vivo component or device applications; whereas the boroaluminate sealing-glass compositions of Table 3 are much less favorable for in vivo applications due to their poorer aqueous durabilities.

The matter set forth in the foregoing description and accompanying drawings is offered by way of illustration only and not as a limitation. Other applications and variations of the titanium sealing-glass compositions and glass-to-metal seals formed therefrom will become evident to those skilled in the art. In particular, the titanium sealing-glass compositions of the present invention have applications for forming glass-to-metal seals for electrical feedthroughs for many types of devices for including implantable devices such as batteries, heart pacemakers, defibrillators, pumps or the like. The actual scope of the invention is intended to be defined in the following claims when viewed in their proper perspective based on the prior art.

What is claimed is:

1. A sealing-glass composition for forming a glass-to-metal seal with titanium or a titanium alloy, comprising:
   40–70 mole-% B$_2$O$_3$;
   5–30 mole-% BaO;
   5–20 mole-% La$_2$O$_3$; and
   at least one oxide selected from the group consisting of:
      Al$_2$O$_3$ in the amount of 0–20 mole-%;
      CaO in the amount of 0–12 mole-%;
      Li$_2$O in the amount of 0–8 mole-%;
      Na$_2$O in the amount of 0–8 mole-%;
      SiO$_2$ in the amount of 0–8 mole-%; and
      TiO$_2$ in the amount of 0–15 mole-%.

2. A glass-to-metal seal comprising the sealing-glass composition of claim 1 in contact with a metal selected from the group consisting of titanium and titanium alloys.

3. The sealing-glass composition of claim 1 further having a sealing temperature of about 900° C. or less.

4. The sealing-glass composition of claim 1 further having a coefficient of thermal expansion in the range of about 70×$10^{-7}$° C.$^{-1}$ to about 100×$10^{-7}$° C.$^{-1}$.

5. The sealing-glass composition of claim 1 further being substantially resistant to chemical attack upon exposure to water.

6. The sealing-glass composition of claim 1 wherein all percentages total 100.

7. The sealing-glass composition of claim 1 wherein:
$B_2O_3$ is present in the amount of about 44–65 mole-%;
BaO is present in the amount of about 9–21 mole-%;
$La_2O_3$ is present in the amount of about 5–10 mole-%; and
$Li_2O$ is present in the amount of about 3–5 mole-%.

8. The sealing-glass composition of claim 1 wherein:
$B_2O_3$ is present in the amount of about 63 mole-%;
BaO is present in the amount of about 21 mole-%;
$La_2O_3$ is present in the amount of about 5 mole-%;
$Al_2O_3$ is present in the amount of about 5 mole-%;
$Li_2O$ is present in the amount of about 3 mole-%; and
$Na_2O$ is present in the amount of about 3 mole-%.

9. The sealing-glass composition of claim 1 wherein:
$B_2O_3$ is present in the amount of about 65 mole-%;
BaO is present in the amount of about 15 mole-%;
$La_2O_3$ is present in the amount of about 10 mole-%;
$Li_2O$ is present in the amount of about 5 mole-%; and
$SiO_2$ is present in the amount of about 5 mole-%.

10. The sealing-glass composition of claim 1 wherein:
$B_2O_3$ is present in the amount of about 44 mole-%;
BaO is present in the amount of about 9 mole-%;
$La_2O_3$ is present in the amount of about 10 mole-%;
$Al_2O_3$ is present in the amount of about 10 mole-%;
CaO is present in the amount of about 9 mole-%;
$Li_2O$ is present in the amount of about 5 mole-%;
$SiO_2$ is present in the amount of about 2 mole-%; and
$TiO_2$ is present in the amount of about 11 mole-%.

11. The sealing-glass composition of claim 1 wherein:
$B_2O_3$ is present in the amount of about 55 mole-%;
BaO is present in the amount of about 20 mole-%;
$La_2O_3$ is present in the amount of about 5 mole-%;
$Al_2O_3$ is present in the amount of about 5 mole-%;
$Li_2O$ is present in the amount of about 5 mole-%;
$Na_2O$ is present in the amount of about 5 mole-%; and
$TiO_2$ is present in the amount of about 5 mole-%.

12. The sealing-glass composition of claim 1 wherein:
$B_2O_3$ is present in the amount of about 54 mole-%;
BaO is present in the amount of about 9 mole-%;
$La_2O_3$ is present in the amount of about 8 mole-%;
$Al_2O_3$ is present in the amount of about 4 mole-%;
CaO is present in the amount of about 9 mole-%;
$Li_2O$ is present in the amount of about 5 mole-%; and
$TiO_2$ is present in the amount of about 11 mole-%.

13. A glass-to-metal seal comprising:
a metal consisting of titanium or a titanium alloy; and
a sealing-glass in contact with the metal and further comprising:
40–70 mole-% $B_2O_3$;
5–30 mole-% BaO;
5–20 mole-% $La_2O_3$; and
at least one oxide selected from the group consisting of:
$Al_2O_3$ in the amount of 0–20 mole-%;
CaO in the amount of 0–12 mole-%;
$Li_2O$ in the amount of 0–8 mole-%;
$Na_2O$ in the amount of 0–8 mole-%;
$SiO_2$ in the amount of 0–8 mole-%; and
$TiO_2$ in the amount of 0–15 mole-%.

14. The glass-to-metal seal of claim 13 further having a sealing temperature of less than about 900° C.

15. The glass-to-metal seal of claim 13 wherein all percentages total 100.

16. The glass-to-metal seal of claim 13 further having a coefficient of thermal expansion in the range of about $70 \times 10^{-7}$° $C.^{-1}$ to about $100 \times 10^{-7}$° $C.^{-1}$.

17. The glass-to-metal seal of claim 13 further being substantially resistant to chemical attack upon exposure to water.

18. An electrical feedthrough for use in an implantable device, comprising:
a sealing-glass composition in contact with titanium or a titanium alloy and including:
40–70 mole-% $B_2O_3$;
5–30 mole-% BaO;
5–20 mole-% $La_2O_3$; and
at least one oxide selected from the group consisting of:
$Al_2O_3$ in the amount of 0–20 mole-%;
CaO in the amount of 0–12 mole-%;
$Li_2O$ in the amount of 0–8 mole-%;
$Na_2O$ in the amount of 0–8 mole-%;
$SiO_2$ in the amount of 0–8 mole-%; and
$TiO_2$ in the amount of 0–15 mole-%.

19. The electrical feedthrough of claim 18 wherein the implantable device is selected from the group consisting of batteries, heart pacemakers, defibrillators, and pumps.

* * * * *